US005624416A

United States Patent [19]

Schatz

[11] Patent Number: 5,624,416

[45] Date of Patent: Apr. 29, 1997

[54] DEVICE FOR CLEANING SKIN PORES

[76] Inventor: Viktor Schatz, Deutschherranstrasse 92, D-53177 Bonn, Germany

[21] Appl. No.: 373,242

[22] PCT Filed: Jul. 15, 1993

[86] PCT No.: PCT/EP93/01856

§ 371 Date: Jan. 17, 1995

§ 102(e) Date: Jan. 17, 1995

[87] PCT Pub. No.: WO94/02186

PCT Pub. Date: Feb. 3, 1994

[30] Foreign Application Priority Data

Jul. 17, 1992 [DE] Germany .......................... 42 23 516.2

[51] Int. Cl.$^6$ ............................ A61M 1/00; A61M 35/00

[52] U.S. Cl. ........................... 604/313; 604/289; 604/290

[58] Field of Search .................................... 604/289, 290, 604/313–315, 292, 293, 316; 294/2

[56] References Cited

U.S. PATENT DOCUMENTS

| | | | |
|---|---|---|---|
| 1,847,619 | 3/1932 | Mascolo . | |
| 2,338,339 | 1/1944 | Mere et al. | 604/315 |
| 3,315,665 | 4/1967 | MacLeod et al. | 604/315 |
| 4,295,243 | 10/1981 | King . | |
| 4,611,397 | 9/1986 | Janisiewicz et al. | 294/2 |

*Primary Examiner*—John G. Weiss
*Assistant Examiner*—Dennis Ruhl
*Attorney, Agent, or Firm*—Herbert Dubno

[57] ABSTRACT

Described is a suction device for cleaning the skin, the device having a suction nozzle with several openings, plus a gap. The skin is drawn by a pulsating suction force into the openings where it closes off the gap in which a pulsating compression force synchronized with the suction force is generated. Comedones are thus squeezed out of the pores by short, variable compressive thrusts.

6 Claims, 5 Drawing Sheets

DEVICE FOR CLEANING SKIN PORES

CROSS REFERENCE TO RELATED APPLICATIONS

This application is a national phase of PCT/EP 93/01856 filed 15 Jul. 1993 and based in turn on German national application P 42 23 516.2 of 17 Jul. 1992 under the International Convention.

FIELD OF THE INVENTION

The invention relates to a mechanical device for cleaning skin pores from sebum, dirt and bacteria deposited in the pores, so called white and black comedones, thereby eliminating their effects in the form of pimples and blackheads.

BACKGROUND OF THE INVENTION

It is very common in skin care to remove impurities, sebum residues lodged in the skin pores, etc. These residues very often clog the pores, hinder cutaneous breathing, collect bacteria and cause pimples or acne. In addition to a series of medicated preparations, there are also treatments with comedone extractors, which require use only by a skilled person and which can be quite time-consuming. These treatments are used when the condition is advanced and can produce visible, unpleasant results. It is also important to regularly clean the pores, even when the skin is healthy and the skin glands function normally, which can be done by washing, face masks and steam baths. A series of known publications also propose treatments based on the use of vacuum for the removal of impurities from the skin pores. There are products on the market which, although widely used, cannot fulfill the promises of effective cleaning.

A series of suction devices based on vacuum are known such as described in the following references: FR-26 26 179; U.S. Pat. Nos. 4,292,971; 4,900,316; 3,794,035; DE 26 11 721; U.S. Pat. No. 4,609,368; DE 32 16 523 A1; AB 353 395; U.S. Pat. Nos. 722,019; 948,005; 1,141,373; 1,225,244; 2,571,398; 4,141,379; 4,765,316, which in various ways propose to remove the skin and pore substances through suction and are here cited as technological background.

The above-mentioned techniques all have a common disadvantage in that the practical cleansing effect is minimal or nonexistent. This can be explained by the fact that although the pores are opened, the suction is made more difficult because the pore remains closed on the body side.

DE 40 29 326 and related literature represent a substantial advance in this field, in that they use pulse action to prevent bruises and apply an elastic membrane to the suction nozzle, which is common to a number of suction openings, thereby providing an effective hygiene protection, as well as underpressure distribution to the suction openings. The inside of the suction device is safely protected from the penetration of extracted substances, which allows for a more compact construction.

OBJECT OF THE INVENTION

It is the object of the present invention to provide an improved method of and apparatus for the cleaning of skin pores, especially for removing clogs formed by sebum depositions, comedones, etc., thereby also safely preventing any damage to the skin.

SUMMARY OF THE INVENTION

These objects are achieved, in accordance with the invention, in that the skin portions subjected suction, preferably according to DE 40 29 326, are also subjected to a mechanical pressure effect in the lower region of the lifted skin portion, which then results in a pressing out of the pore contents.

The suction of the skin into the nozzle opening serves exclusively for drawing the pore into an advantageous position in order to open it, after which the pressure effect all around the pore is the actual effectively applied cleaning force.

According to the present invention, the pressure effect is further subdivided into short pressure pulses, whose time and amplitude parameters are varied so that an optimal cleaning can be obtained while bruising is prevented.

According to the invention, during one suction interval, several pressure pulses are applied. To produce these pressure pulses which are shorter than a suction interval, I may superimpose vibrations (with incomplete amplitude decrease) upon a main pressure pulse. These finer harmonic vibrations of the pressure force cause loosening of the skin-pore-sebum system, making membrane, nozzle walls-pressure-generating elements or media and the substances pressed out from the pores "flow" much easier.

Preferably in the suction nozzles contain several small suction openings with a narrow gap, so that the nozzle is subdivided into two superimposed disks, having suction openings arranged on top of each other. The narrow gap is attached to a channel and connected with the pressure generator, while the openings of the suction openings are connected to a underpressure generator. The vacuum effect is applied first and aspires some of the (relaxed) pressure medium from the gap, while at the same time it pulls the skin into the suction openings, which in turn close the narrow gap when the depths corresponding to the gap is reached (by a valve effect). Subsequently the pressure is built up in the gap. The pressure acts on the skin pore pressing out the deposits which have formed there. Compressed air which is controlled by an electromagnetically actuated valve, is the advantageous pressure medium.

A liquid medium can be used as the medium for suction and pressure effects. The liquid medium is preferably water. A hydraulic control unit is controlled in such a way that besides the above-described flow parameters, the losses of liquid through the open suction openings are also taken into account and corrected by influx.

The mechanical force on the pore can be supplied by movable parts. For example, two plier-like pressure pieces are connected to a unit by an articulated hinge, and the channel formed by the two parts is connected to the suction unit via a control valve. The movable plier part is preferably actuated by an electromagnet. The shape and surface structure of the two pressure pieces are designed so that the skin treatment can be performed as gently as possible. This means that the possible largest surface contact with the skin portions to be treated should be used for low surface pressure values, and rounded edges should be provided to guard against imprints on the skin. In order to combine several small suction-pressure units with only one movable part, the pressure pieces are extended lengthwise and are subdivided with small inserts.

Besides all previously described flow parameters, this construction allows for additional control of the gap width between the two pressure pieces, which facilitates the adjustment to skin types of various thickness and elasticity.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
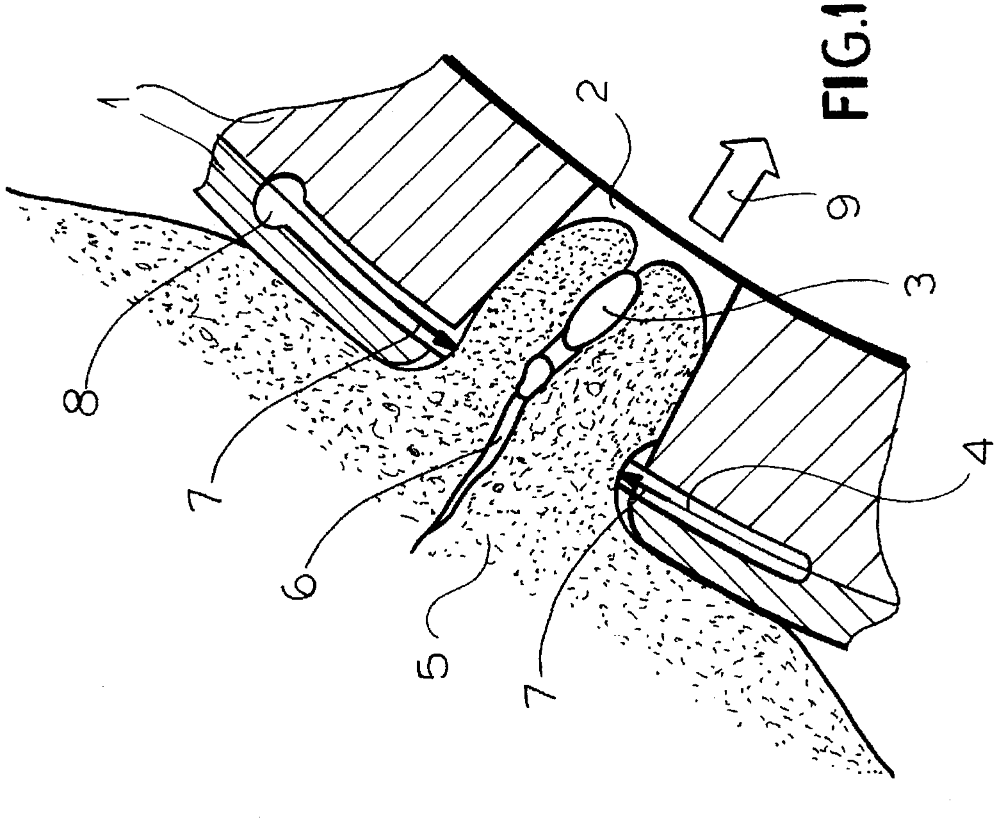
FIG. 1 is a diagrammatic section showing a suction opening with a skin pore subjected to suction and the gap for the acting force.

In FIG. 1 a highly enlarged illustration of a skin pore 6 with a comedone 3 is shown in the position when it is sucked into the suction opening 2. The inner channel of the suction opening 2 is connected to the underpressure generator 9 together with other suction openings. The nozzle body consists of two superimposed disks 1, which define a gap 4 between them, which surrounds the suction opening and is connected to a pressure generator (not shown in the drawing) by means of channel 8.

Shortly after a suction pulse, when the skin is pulled into the suction opening 2, whereby the lateral gap 4 is closed off by the skin (valve effect), the pressure pulse 7 is given to the gap and squeezes the sucked-in skin portion. Thereby the content of the pore, if a pore is seized, is pressed out. It is also advantageous for the sucked-in skin to slip out due to the suction loss.

The pressure medium in gap 4, as well as the suction medium in the nozzle chamber 9 can be compressed air or even a liquid medium when a harder (steepness of curve slope) action is required.

The liquid will act the same way on the skin pores through the suction openings 2 and the gap 4, due to the pressure control in gap 4 and the underpressure in the nozzle chamber 9. Some liquid will always be discharged, and will have to be replenished constantly by supply, which can be done through correspondingly defined control. This also has in addition the side-effect of rinsing away the aspired substances and results in a practical and hygienic device, which however will be limited to use in bathrooms or washrooms, since its preferred medium is water.

Figure 2:
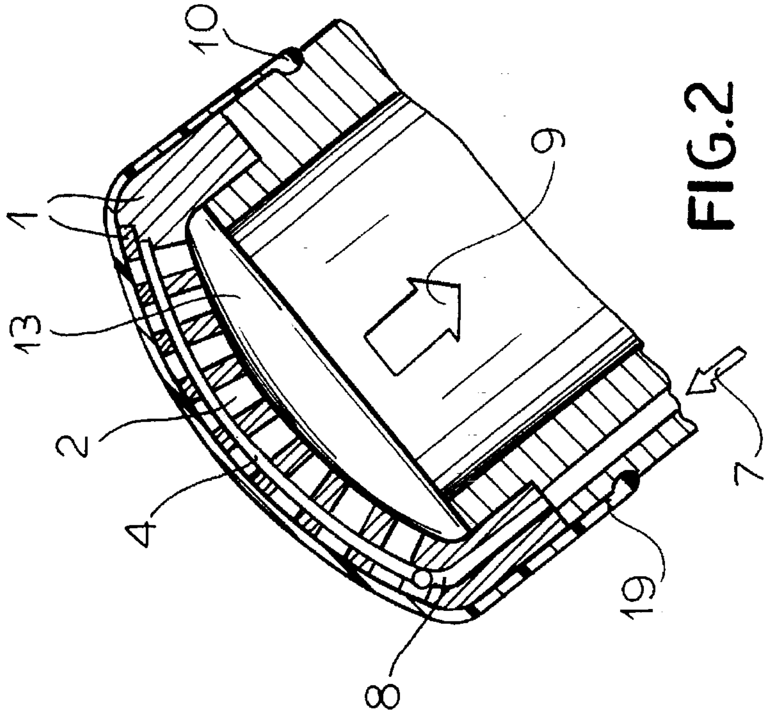
FIG. 2 is a cross section through the suction nozzle.

FIG. 2 shows a cross section through a suction pressure nozzle with several suction openings 2 according to FIG. 1. The annular groove 10 indicates the use of the elastic membrane 19 according to DE-40 29 326.

Figure 3:
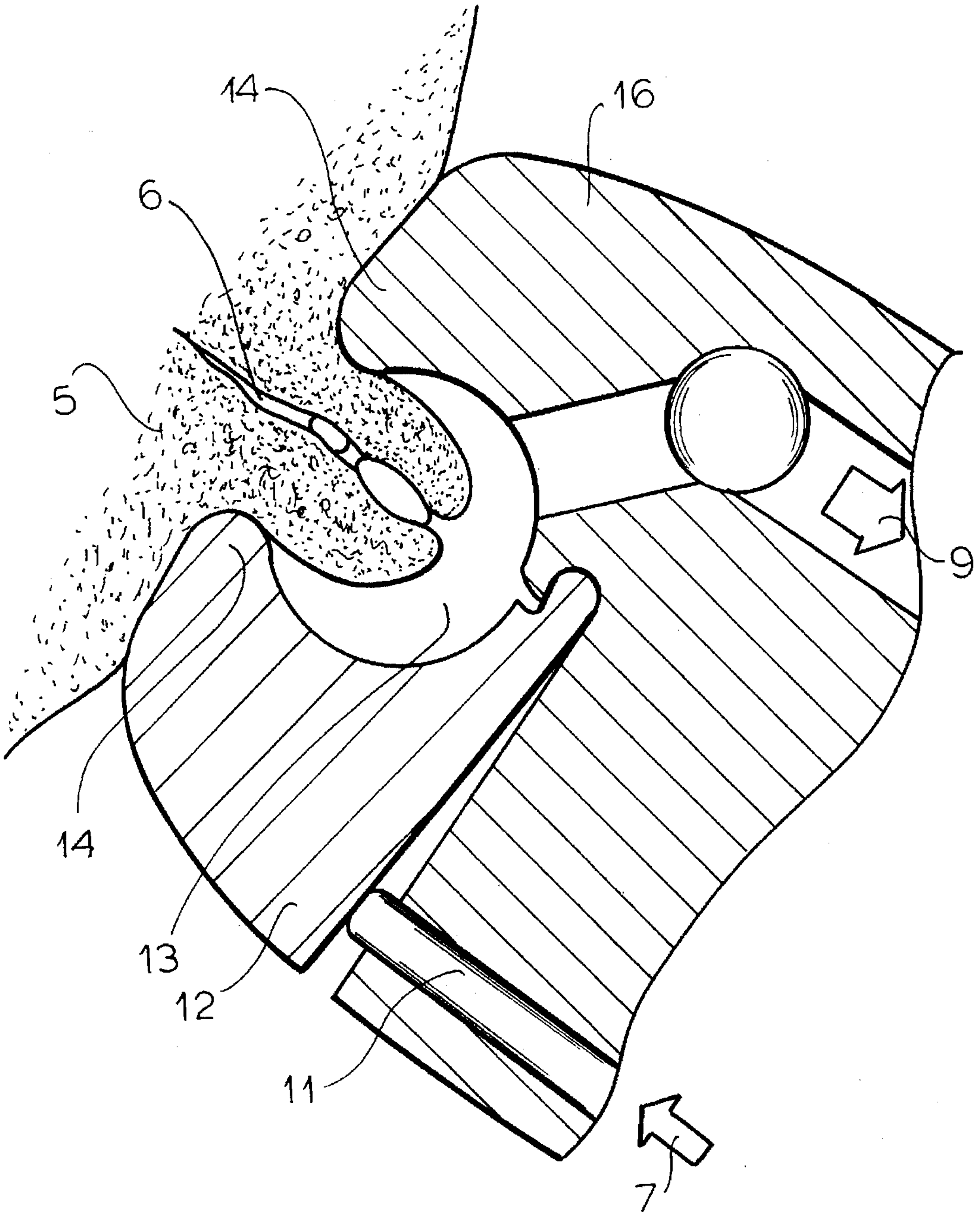
FIG. 3 is a section of the suction nozzle in a plier shape for the application of mechanical force.

A further advantageous mechanical solution is shown in FIG. 3, whereby the sucked-in skin portion surrounded in a plier-like manner by the two or more lips 14, surrounding and at the same time forming the suction openings is pressed together for a short pulse with predetermined pressure and motion path.

Figure 4:
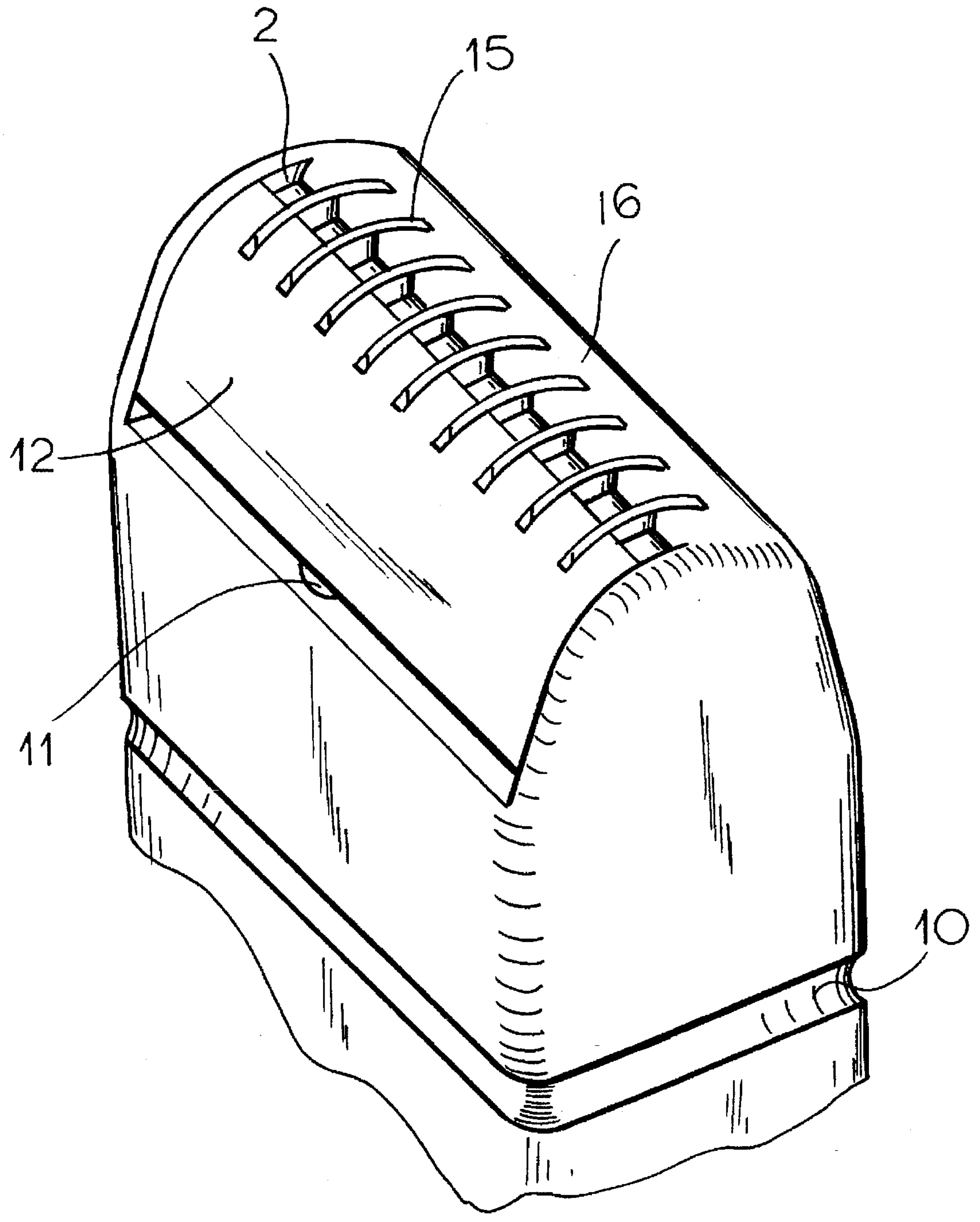
FIG. 4 is a top view of the suction nozzle in a plier-shape.

FIG. 4 shows a lengthwise extending suction-pressure nozzle, which makes possible to limit the device to only one movable part 12. The nozzle contains divider sheets 15 which subdivide the same into several smaller suction openings 2. This subdivision into several smaller suction openings has its advantages when an elastic membrane 19 according to DE-40 29 326 is pulled over the nozzle, whereby then the underpressure distribution to all suction openings is insured even when one or more of them are not closed by skin contact.

Figure 5:
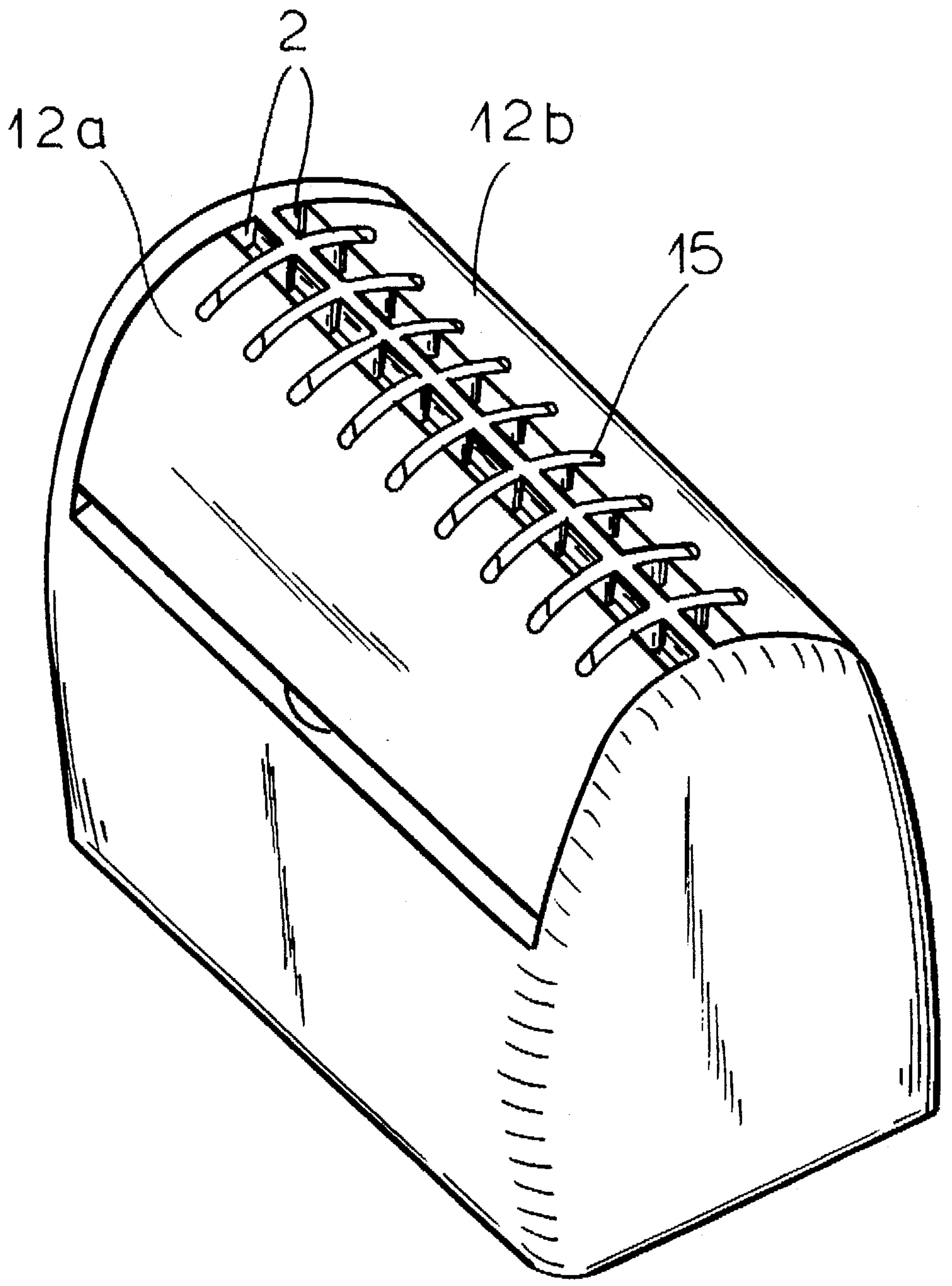
FIG. 5 is a top view of the suction nozzle in a plier shape with two movable pressure pieces.

FIG. 5 shows an advantageous further development of the construction according to FIG. 3 and FIG. 4, whereby here two rows of suction openings are created due to the use of two movable parts **12*a* and 12*b* and the rigid consolidation of the divider sheets into one divider 15. The possible and advantageous embodiment with (not illustrated) staggered rows of suction openings 2 and with a floatingly supported divider 15** has also to be added.

The optimal effect with the exclusion of skin damage is achieved through the proper selection of the pressure amplitude $P_1$, duration and pressure effect 17 with the amplitude $P_H$. The period T is initiated by the start of the suction effect 18, which here through steep curve slopes corresponding to the reality takes a certain time. After a suction time $_{ta}$ the skin is sucked in and the pressure action 17 is triggered. For the predetermined, experimentally established time both control signal remain active, after which a rest phase is initiated for the time $t_r$.

Figure 6:
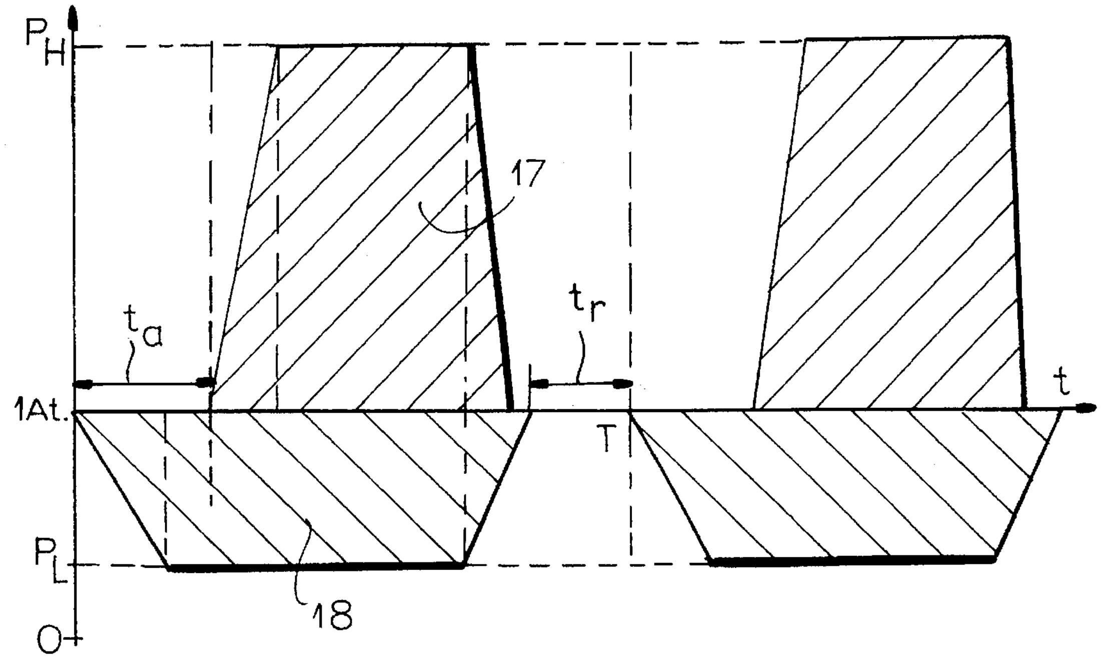
FIG. 6 is a control diagram of the suction and pressure pulses.
Figure 7:
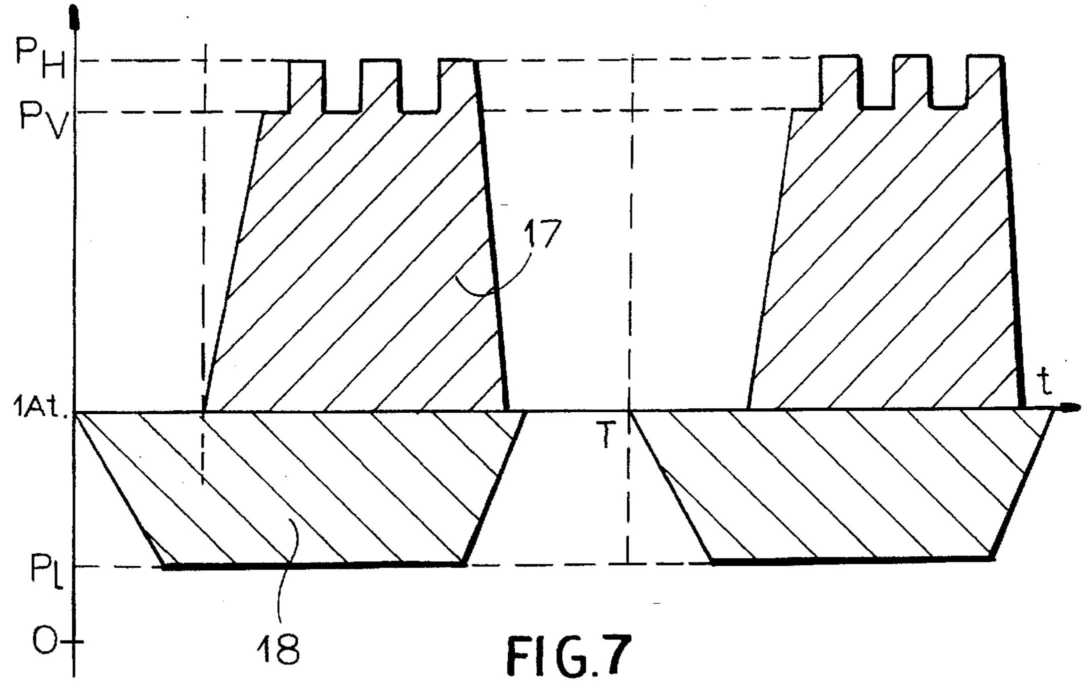
FIG. 7 is a control diagram of the suction and pressure pulses with superimposed pressure vibrations.

In addition to the signal curve shown in FIG. 6, FIG. 7 shows an oscillation superimposed on pressure action 17, which is represented by the amplitude difference ($P_H$-$P_V$).

The described device with several advantageous embodiments encourages the development of other constructive solutions for implementing the main concept. Besides the pore-cleaning effect, a construction developed according to the invention can also have the additional side effect of thoroughly massaging the treated skin in a new manner, which contributes positively to the supply of nutrients to the skin cells. When one thinks that a cosmetic skin cleaning is more often desired by consumers, such a thorough massage would also be performed automatically at the same time, and such regularity would lead to better treatment results, this way the skin health and vitality being preserved for a longer period of time.

I claim:

1. A device for cleaning skin pores of the skin of a person to be treated which comprises:

a pair of jaws relatively movable to spread said jaws apart and cause said jaws to approach one another;

a suction source for applying suction between said jaws, thereby drawing a skin pore between said jaws when said jaws are spread apart; and means for pressing said jaws against said skin and squeezing contaminants from said skin pore, said suction force being pulsed to massage said skin with repetitive drawing of skin pores between said jaws and the squeezing of contaminants therefrom as said device is moved on the skin of the person, said jaws defining a slot between them, said slot being formed with spaced-apart chambers to which suction is applied and for receiving respective pores of the skin.

2. A device for cleaning skin pores of the skin of a person to be treated which comprises:

a pair of jaws relatively movable to spread said jaws apart and cause said jaws to approach one another;

a suction source for applying suction between said jaws, thereby drawing a skin pore between said jaws when said jaws are spread apart; and means for pressing said jaws against said skin and squeezing contaminants from said skin pore, said suction force being pulsed to massage said skin with repetitive drawing of skin pores between said jaws and the squeezing of contaminants therefrom as said device is moved on the skin of the person, round suction openings being formed between said jaws to receive respective skin pores.

3. A device for cleaning skin pores of the skin of a person to be treated which comprises:

a pair of jaws relatively movable to spread said jaws apart and cause said jaws to approach one another;

a suction source for applying suction between said jaws, thereby drawing a skin pore between said jaws when said jaws are spread apart;

means for pressing said jaws against said skin and squeezing contaminants from said skin pore, said suction force being pulsed to massage said skin with repetitive drawing of skin pores between said jaws and the squeezing of contaminants therefrom as said device is moved on the skin of the person; and an elastic membrane to be interposed between said skin pore and said jaws.

4. The device defined in claim 3 wherein one of said jaws is formed with a hinge enabling displacement of said one of said jaws relative to the other of said jaws.

5. A method of cleaning skin pores, comprising the steps of:

(a) pressing two relatively movable jaws against skin of a person to be treated, and applying suction to the skin between said jaws in a spread-apart state thereof, thereby drawing a skin pore to be cleaned between the two relatively movable jaws in the spread-apart state;

(b) while said skin pore is between said jaws, forcing said jaws together to force contaminants from said skin pore;

(c) thereafter spreading said jaws apart to release said skin pore; and (d) repeating steps (a) through (c) with pulsing of said suction and movement of said jaws over skin to be treated, thereby massaging the skin.

6. The method defined in claim 5, further comprising the steps of interposing a diaphragm between said jaws and the skin of the person to be treated so that each skin pore is drawn together with a portion of said diaphragm between said jaws.

* * * * *